US008886317B2

(12) United States Patent
Cooke et al.

(10) Patent No.: US 8,886,317 B2
(45) Date of Patent: *Nov. 11, 2014

(54) MRI OPERATION MODES FOR IMPLANTABLE MEDICAL DEVICES

(71) Applicant: Cardiac Pacemakers, Inc., St. Paul, MN (US)

(72) Inventors: Daniel J. Cooke, Roseville, MN (US); Jeffrey A. Von Arx, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/027,812

(22) Filed: Sep. 16, 2013

(65) Prior Publication Data

US 2014/0018870 A1    Jan. 16, 2014

Related U.S. Application Data

(60) Continuation of application No. 13/178,571, filed on Jul. 8, 2011, now Pat. No. 8,543,207, which is a division of application No. 11/015,807, filed on Dec. 17, 2004, now Pat. No. 8,014,867.

(51) Int. Cl.
*A61N 1/37* (2006.01)
*A61N 1/39* (2006.01)
*A61N 1/368* (2006.01)
*A61N 1/02* (2006.01)

(52) U.S. Cl.
CPC ............ *A61N 1/3718* (2013.01); *A61N 1/3931* (2013.01); *A61N 1/3688* (2013.01); *Y10S 128/901* (2013.01); *A61N 1/3692* (2013.01); *A61N 1/02* (2013.01)
USPC ................ 607/31; 607/27; 600/411; 128/901

(58) Field of Classification Search
USPC .......... 607/9, 27, 30, 31, 60; 600/411; 128/31
See application file for complete search history.

(56) References Cited

U.S. PATENT DOCUMENTS 3,888,260 A   6/1975  Fischell
3,898,995 A   8/1975  Dresbach (Continued)

FOREIGN PATENT DOCUMENTS

EP    0530006 A1    3/1993
EP    0591334 A1    4/1994

(Continued)

OTHER PUBLICATIONS

Dempsey Mary F. et al., "Investigation of the Factors Responsible for Burns During MRI", Journal of Resonance Imaging 2001;13;627-631.

(Continued)

*Primary Examiner* — Rex R Holmes
(74) *Attorney, Agent, or Firm* — Faegre Baker Daniels LLP

(57) ABSTRACT

One embodiment of the present invention relates to an implantable medical device ("IMD") that can be programmed from one operational mode to another operational mode when in the presence of electro-magnetic interference ("EMI"). In accordance with this particular embodiment, the IMD includes a communication interface for receiving communication signals from an external device, such as a command to switch the IMD from a first operation mode to a second operation mode. The IMD further includes a processor in electrical communication with the communication interface, which is operable to switch or reprogram the IMD from the first operation mode to the second operation mode upon receiving a command to do so. In addition, the IMD includes a timer operable to measure a time period from when the processor switches the IMD to the second operation mode. In accordance with this aspect of the invention, the processor is in electrical communication with the timer, and is further operable to switch the IMD from the second operation mode back to the first operation mode when the measured time period reaches a predetermined time period.

20 Claims, 9 Drawing Sheets

(56) References Cited

U.S. PATENT DOCUMENTS

| | | |
|---|---|---|
| 4,091,818 A | 5/1978 | Brownlee et al. |
| 4,379,459 A | 4/1983 | Stein |
| 4,404,125 A | 9/1983 | Abolins et al. |
| 4,516,579 A | 5/1985 | Irnich |
| 4,611,127 A | 9/1986 | Ibrahim et al. |
| 4,694,837 A | 9/1987 | Blakeley et al. |
| 4,729,376 A | 3/1988 | DeCote, Jr. |
| 4,751,110 A | 6/1988 | Gulla et al. |
| 4,779,617 A | 10/1988 | Whigham |
| 4,823,075 A | 4/1989 | Alley |
| 4,869,970 A | 9/1989 | Gulla et al. |
| 4,934,366 A | 6/1990 | Truex et al. |
| 5,038,785 A | 8/1991 | Blakeley et al. |
| 5,075,039 A | 12/1991 | Goldberg |
| 5,076,841 A | 12/1991 | Chen et al. |
| 5,120,578 A | 6/1992 | Chen et al. |
| 5,181,511 A | 1/1993 | Nickolls et al. |
| 5,187,136 A | 2/1993 | Klobucar et al. |
| 5,188,117 A | 2/1993 | Steinhaus et al. |
| 5,197,468 A | 3/1993 | Proctor et al. |
| 5,217,010 A | 6/1993 | Tsitlik et al. |
| 5,243,911 A | 9/1993 | Dow et al. |
| 5,279,225 A | 1/1994 | Dow et al. |
| 5,288,313 A | 2/1994 | Portner |
| 5,292,342 A | 3/1994 | Nelson et al. |
| 5,309,096 A | 5/1994 | Hoegnelid |
| 5,325,728 A | 7/1994 | Zimmerman et al. |
| 5,345,362 A | 9/1994 | Winkler |
| 5,391,188 A | 2/1995 | Nelson et al. |
| 5,406,444 A | 4/1995 | Selfried et al. |
| 5,424,642 A | 6/1995 | Ekwall |
| 5,438,900 A | 8/1995 | Sundstrom |
| 5,454,837 A | 10/1995 | Lindegren et al. |
| 5,470,345 A | 11/1995 | Hassler et al. |
| 5,523,578 A | 6/1996 | Herskovic |
| 5,527,348 A | 6/1996 | Winkler et al. |
| 5,529,578 A | 6/1996 | Struble |
| 5,545,187 A | 8/1996 | Bergstrom et al. |
| 5,562,714 A | 10/1996 | Grevious |
| 5,607,458 A | 3/1997 | Causey, III et al. |
| 5,609,622 A | 3/1997 | Soukup et al. |
| 5,618,208 A | 4/1997 | Crouse et al. |
| 5,620,476 A | 4/1997 | Truex et al. |
| 5,647,379 A | 7/1997 | Meltzer |
| 5,649,965 A | 7/1997 | Pons et al. |
| 5,650,759 A | 7/1997 | Hittman et al. |
| 5,662,694 A | 9/1997 | Lidman et al. |
| 5,662,697 A | 9/1997 | Li et al. |
| 5,683,434 A | 11/1997 | Archer |
| 5,687,735 A | 11/1997 | Forbes et al. |
| 5,694,952 A * | 12/1997 | Lidman et al. ............... 128/899 |
| 5,697,958 A | 12/1997 | Paul et al. |
| 5,709,225 A | 1/1998 | Budgifvars et al. |
| 5,714,536 A | 2/1998 | Ziolo et al. |
| 5,722,998 A | 3/1998 | Prutchi et al. |
| 5,727,552 A | 3/1998 | Ryan |
| 5,735,884 A | 4/1998 | Thompson et al. |
| 5,749,910 A | 5/1998 | Brumwell et al. |
| 5,751,539 A | 5/1998 | Stevenson et al. |
| 5,759,197 A | 6/1998 | Sawchuk et al. |
| 5,764,052 A | 6/1998 | Renger |
| 5,766,227 A | 6/1998 | Nappholz et al. |
| 5,776,168 A | 7/1998 | Gunderson |
| 5,782,241 A | 7/1998 | Felblinger et al. |
| 5,782,891 A | 7/1998 | Hassler et al. |
| 5,792,201 A | 8/1998 | Causey, III et al. |
| 5,800,496 A | 9/1998 | Swoyer et al. |
| 5,800,497 A | 9/1998 | Bakels et al. |
| 5,814,090 A | 9/1998 | Latterell et al. |
| 5,817,130 A | 10/1998 | Cox et al. |
| 5,827,997 A | 10/1998 | Chung et al. |
| 5,853,375 A | 12/1998 | Orr |
| 5,867,361 A | 2/1999 | Wolf et al. |
| 5,869,078 A | 2/1999 | Baudino |
| 5,870,272 A | 2/1999 | Seifried et al. |
| 5,871,509 A | 2/1999 | Noren |
| 5,877,630 A | 3/1999 | Kraz |
| 5,895,980 A | 4/1999 | Thompson |
| 5,905,627 A | 5/1999 | Brendel et al. |
| 5,959,829 A | 9/1999 | Stevenson et al. |
| 5,964,705 A | 10/1999 | Truwit et al. |
| 5,968,854 A | 10/1999 | Akopian et al. |
| 5,973,906 A | 10/1999 | Stevenson et al. |
| 5,978,204 A | 11/1999 | Stevenson |
| 5,978,710 A | 11/1999 | Prutchi et al. |
| 5,999,398 A | 12/1999 | Makl et al. |
| 6,008,980 A | 12/1999 | Stevenson et al. |
| 6,031,710 A | 2/2000 | Wolf et al. |
| 6,032,063 A | 2/2000 | Hoar et al. |
| 6,055,455 A | 4/2000 | O'Phelan et al. |
| 6,079,681 A | 6/2000 | Stern et al. |
| 6,101,417 A | 8/2000 | Vogel et al. |
| 6,147,301 A | 11/2000 | Bhatia |
| 6,161,046 A | 12/2000 | Maniglia et al. |
| 6,162,180 A | 12/2000 | Miesel et al. |
| 6,173,203 B1 | 1/2001 | Barkley et al. |
| 6,188,926 B1 | 2/2001 | Vock |
| 6,192,279 B1 | 2/2001 | Barreras, Sr. et al. |
| 6,198,968 B1 | 3/2001 | Prutchi et al. |
| 6,198,972 B1 | 3/2001 | Hartlaub et al. |
| 6,209,764 B1 | 4/2001 | Hartlaub et al. |
| 6,217,800 B1 | 4/2001 | Hayward |
| 6,235,038 B1 | 5/2001 | Hunter et al. |
| 6,245,464 B1 | 6/2001 | Spillman et al. |
| 6,246,902 B1 | 6/2001 | Naylor et al. |
| 6,249,701 B1 | 6/2001 | Rajasekhar et al. |
| 6,268,725 B1 | 7/2001 | Vernon et al. |
| 6,270,831 B2 | 8/2001 | Kumar et al. |
| 6,275,369 B1 | 8/2001 | Stevenson et al. |
| 6,288,344 B1 | 9/2001 | Youker et al. |
| 6,324,431 B1 | 11/2001 | Zarinetchi et al. |
| 6,358,281 B1 | 3/2002 | Berrang et al. |
| 6,365,076 B1 | 4/2002 | Bhatia |
| 6,381,494 B1 | 4/2002 | Gilkerson et al. |
| 6,421,555 B1 | 7/2002 | Nappholz |
| 6,424,234 B1 | 7/2002 | Stevenson |
| 6,446,512 B2 | 9/2002 | Zimmerman et al. |
| 6,452,564 B1 | 9/2002 | Schoen et al. |
| 6,456,481 B1 | 9/2002 | Stevenson |
| 6,459,935 B1 | 10/2002 | Piersma |
| 6,470,212 B1 | 10/2002 | Weijand et al. |
| 6,487,452 B2 | 11/2002 | Legay |
| 6,490,148 B1 | 12/2002 | Allen et al. |
| 6,496,714 B1 | 12/2002 | Weiss et al. |
| 6,503,964 B2 | 1/2003 | Smith et al. |
| 6,506,972 B1 | 1/2003 | Wang |
| 6,510,345 B1 | 1/2003 | Van Bentem |
| 6,512,666 B1 | 1/2003 | Duva |
| 6,522,920 B2 | 2/2003 | Silvian et al. |
| 6,526,321 B1 | 2/2003 | Spehr |
| 6,539,253 B2 | 3/2003 | Thompson et al. |
| 6,545,854 B2 | 4/2003 | Trinh et al. |
| 6,555,745 B1 | 4/2003 | Kruse et al. |
| 6,563,132 B1 | 5/2003 | Talroze et al. |
| 6,566,978 B2 | 5/2003 | Stevenson et al. |
| 6,567,259 B2 | 5/2003 | Stevenson et al. |
| 6,580,947 B1 | 6/2003 | Thompson |
| 6,584,351 B1 | 6/2003 | Ekwall |
| 6,595,756 B2 | 7/2003 | Gray et al. |
| 6,607,485 B2 | 8/2003 | Bardy |
| 6,626,937 B1 | 9/2003 | Cox |
| 6,629,938 B1 | 10/2003 | Engvall et al. |
| 6,631,290 B1 | 10/2003 | Guck et al. |
| 6,631,555 B1 | 10/2003 | Youker et al. |
| 6,640,137 B2 | 10/2003 | MacDonald |
| 6,643,903 B2 | 11/2003 | Stevenson et al. |
| 6,646,198 B2 | 11/2003 | Maciver et al. |
| 6,648,914 B2 | 11/2003 | Berrang et al. |
| 6,662,049 B1 | 12/2003 | Miller |
| 6,673,999 B1 | 1/2004 | Wang et al. |
| 6,711,440 B2 | 3/2004 | Deal et al. |
| 6,713,671 B1 | 3/2004 | Wang et al. |
| 6,718,203 B2 | 4/2004 | Weiner et al. |
| 6,718,207 B2 | 4/2004 | Connelly |

(56) References Cited

U.S. PATENT DOCUMENTS

| | | |
|---|---|---|
| 6,725,092 B2 | 4/2004 | MacDonald et al. |
| 6,731,979 B2 | 5/2004 | MacDonald |
| 6,795,730 B2 | 9/2004 | Connelly et al. |
| 6,901,292 B2 | 5/2005 | Hrdlicka et al. |
| 6,925,328 B2 | 8/2005 | Foster et al. |
| 6,937,906 B2 | 8/2005 | Terry et al. |
| 6,944,489 B2 | 9/2005 | Zeijlemaker et al. |
| 6,963,779 B1 | 11/2005 | Shankar |
| 7,013,180 B2 | 3/2006 | Dublin et al. |
| 7,020,517 B2 | 3/2006 | Weiner |
| 7,050,855 B2 | 5/2006 | Zeijlemaker et al. |
| 7,076,283 B2 | 7/2006 | Cho et al. |
| 7,082,328 B2 | 7/2006 | Funke |
| 7,092,756 B2 | 8/2006 | Zhang et al. |
| 7,123,013 B2 | 10/2006 | Gray |
| 7,138,582 B2 | 11/2006 | Lessar et al. |
| 7,164,950 B2 | 1/2007 | Kroll et al. |
| 7,174,219 B2 | 2/2007 | Wahlstrand et al. |
| 7,174,220 B1 | 2/2007 | Chitre et al. |
| 7,212,863 B2 | 5/2007 | Strandberg |
| 7,231,251 B2 | 6/2007 | Yonce et al. |
| 7,242,981 B2 | 7/2007 | Ginggen |
| 7,272,444 B2 | 9/2007 | Peterson et al. |
| 7,369,898 B1 | 5/2008 | Kroll et al. |
| 7,388,378 B2 | 6/2008 | Gray et al. |
| 7,509,167 B2 | 3/2009 | Stessman |
| 7,561,915 B1 | 7/2009 | Cooke et al. |
| 7,801,625 B2 | 9/2010 | MacDonald |
| 7,835,803 B1 | 11/2010 | Malinowski et al. |
| 7,839,146 B2 | 11/2010 | Gray |
| 8,014,867 B2 | 9/2011 | Cooke et al. |
| 8,032,228 B2 | 10/2011 | Ameri et al. |
| 8,086,321 B2 | 12/2011 | Ameri |
| 8,121,705 B2 | 2/2012 | MacDonald |
| 8,160,717 B2 | 4/2012 | Ameri |
| 8,311,637 B2 | 11/2012 | Ameri |
| 8,543,207 B2 | 9/2013 | Cooke et al. |
| 8,554,335 B2 | 10/2013 | Ameri et al. |
| 8,565,874 B2 | 10/2013 | Stubbs et al. |
| 8,571,661 B2 | 10/2013 | Stubbs et al. |
| 8,639,331 B2 | 1/2014 | Stubbs et al. |
| 2001/0002000 A1 | 5/2001 | Kumar et al. |
| 2001/0006263 A1 | 7/2001 | Hayward |
| 2001/0011175 A1 | 8/2001 | Hunter et al. |
| 2001/0018123 A1 | 8/2001 | Furumori et al. |
| 2001/0025139 A1 | 9/2001 | Pearlman |
| 2001/0037134 A1 | 11/2001 | Munshi |
| 2001/0050837 A1 | 12/2001 | Stevenson et al. |
| 2002/0019658 A1 | 2/2002 | Munshi |
| 2002/0026224 A1 | 2/2002 | Thompson et al. |
| 2002/0038135 A1 | 3/2002 | Connelly et al. |
| 2002/0050401 A1 | 5/2002 | Youker et al. |
| 2002/0072769 A1 | 6/2002 | Silvian et al. |
| 2002/0082648 A1 | 6/2002 | Kramer et al. |
| 2002/0102835 A1 | 8/2002 | Stucchi et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0117314 A1 | 8/2002 | Maciver et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147388 A1 | 10/2002 | Mass et al. |
| 2002/0147470 A1 | 10/2002 | Weiner et al. |
| 2002/0162605 A1 | 11/2002 | Horton et al. |
| 2002/0166618 A1 | 11/2002 | Wolf et al. |
| 2002/0175782 A1 | 11/2002 | Trinh et al. |
| 2002/0183796 A1 | 12/2002 | Connelly |
| 2002/0198569 A1 | 12/2002 | Foster et al. |
| 2003/0036774 A1 | 2/2003 | Maier et al. |
| 2003/0036776 A1 | 2/2003 | Foster et al. |
| 2003/0045907 A1 | 3/2003 | MacDonald |
| 2003/0053284 A1 | 3/2003 | Stevenson et al. |
| 2003/0055457 A1 | 3/2003 | MacDonald |
| 2003/0056820 A1 | 3/2003 | MacDonald |
| 2003/0074029 A1 | 4/2003 | Deno et al. |
| 2003/0081370 A1 | 5/2003 | Haskell et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0083728 A1 | 5/2003 | Greatbatch et al. |
| 2003/0100925 A1 | 5/2003 | Pape et al. |
| 2003/0109901 A1 | 6/2003 | Greatbatch |
| 2003/0111142 A1 | 6/2003 | Horton et al. |
| 2003/0114897 A1 | 6/2003 | Von Arx et al. |
| 2003/0114898 A1 | 6/2003 | Von Arx et al. |
| 2003/0120197 A1 | 6/2003 | Kaneko et al. |
| 2003/0130647 A1 | 7/2003 | Gray et al. |
| 2003/0130700 A1 | 7/2003 | Miller et al. |
| 2003/0130701 A1 | 7/2003 | Miller |
| 2003/0130708 A1 | 7/2003 | Von Arx et al. |
| 2003/0135114 A1 | 7/2003 | Pacetti et al. |
| 2003/0135160 A1 | 7/2003 | Gray et al. |
| 2003/0139096 A1 | 7/2003 | Stevenson et al. |
| 2003/0140931 A1 | 7/2003 | Zeijlemaker et al. |
| 2003/0144704 A1 | 7/2003 | Terry et al. |
| 2003/0144705 A1* | 7/2003 | Funke .................... 607/27 |
| 2003/0144706 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0149459 A1 | 8/2003 | Von Arx et al. |
| 2003/0158584 A1 | 8/2003 | Cates et al. |
| 2003/0176900 A1 | 9/2003 | MacDonald |
| 2003/0179536 A1 | 9/2003 | Stevenson et al. |
| 2003/0191505 A1 | 10/2003 | Gryzwa et al. |
| 2003/0195570 A1 | 10/2003 | Deal et al. |
| 2003/0199755 A1 | 10/2003 | Halperin et al. |
| 2003/0204207 A1 | 10/2003 | MacDonald et al. |
| 2003/0204215 A1 | 10/2003 | Gunderson et al. |
| 2003/0204217 A1 | 10/2003 | Greatbatch |
| 2003/0213604 A1 | 11/2003 | Stevenson et al. |
| 2003/0213605 A1 | 11/2003 | Brendel et al. |
| 2004/0005483 A1 | 1/2004 | Lin |
| 2004/0015162 A1 | 1/2004 | McGaffigan |
| 2004/0015197 A1 | 1/2004 | Gunderson |
| 2004/0019273 A1 | 1/2004 | Helfer et al. |
| 2004/0049237 A1 | 3/2004 | Larson et al. |
| 2004/0088012 A1 | 5/2004 | Kroll et al. |
| 2004/0093432 A1 | 5/2004 | Luo et al. |
| 2004/0263174 A1 | 12/2004 | Gray et al. |
| 2005/0043761 A1 | 2/2005 | Connelly et al. |
| 2005/0070787 A1 | 3/2005 | Zeijlemaker |
| 2005/0070975 A1 | 3/2005 | Zeijlemaker et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0197677 A1 | 9/2005 | Stevenson |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0025820 A1 | 2/2006 | Phillips et al. |
| 2006/0030774 A1 | 2/2006 | Gray et al. |
| 2006/0041294 A1 | 2/2006 | Gray |

(56) References Cited

U.S. PATENT DOCUMENTS

| | | |
|---|---|---|
| 2006/0167496 A1 | 7/2006 | Nelson et al. |
| 2006/0173295 A1 | 8/2006 | Zeijlemaker |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293591 A1 | 12/2006 | Wahlstrand et al. |
| 2007/0019354 A1 | 1/2007 | Kamath |
| 2007/0021814 A1 | 1/2007 | Inman et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0203523 A1 | 8/2007 | Betzold |
| 2007/0238975 A1 | 10/2007 | Zeijlemaker |
| 2007/0255332 A1 | 11/2007 | Cabelka et al. |
| 2008/0033497 A1 | 2/2008 | Bulkes et al. |
| 2008/0132985 A1 | 6/2008 | Wedan et al. |
| 2008/0154342 A1 | 6/2008 | Digby et al. |
| 2008/0221638 A1 | 9/2008 | Wedan et al. |
| 2008/0234772 A1 | 9/2008 | Shuros et al. |
| 2009/0138058 A1 | 5/2009 | Cooke et al. |
| 2009/0149906 A1 | 6/2009 | Ameri et al. |
| 2009/0149909 A1 | 6/2009 | Ameri |
| 2009/0157146 A1 | 6/2009 | Linder et al. |
| 2009/0204182 A1 | 8/2009 | Ameri |
| 2009/0210025 A1 | 8/2009 | Ameri |
| 2010/0087892 A1 | 4/2010 | Stubbs et al. |
| 2010/0211123 A1 | 8/2010 | Stubbs et al. |
| 2011/0137359 A1 | 6/2011 | Stubbs et al. |
| 2011/0270338 A1 | 11/2011 | Cooke et al. |
| 2011/0276104 A1 | 11/2011 | Ameri et al. |
| 2012/0071941 A1 | 3/2012 | Ameri |
| 2012/0253425 A1 | 10/2012 | Yoon et al. |
| 2014/0046390 A1 | 2/2014 | Stubbs et al. |
| 2014/0046392 A1 | 2/2014 | Stubbs et al. |

FOREIGN PATENT DOCUMENTS

| | | |
|---|---|---|
| EP | 0331959 B1 | 12/1994 |
| EP | 0891786 A2 | 1/1999 |
| EP | 0891207 B1 | 11/1999 |
| EP | 0980105 A1 | 2/2000 |
| EP | 0989623 A1 | 3/2000 |
| EP | 0989624 A1 | 3/2000 |
| EP | 1007132 A2 | 6/2000 |
| EP | 1109180 A2 | 6/2001 |
| EP | 1128764 A1 | 9/2001 |
| EP | 0705621 B1 | 1/2002 |
| EP | 1191556 A2 | 3/2002 |
| EP | 1271579 A2 | 1/2003 |
| EP | 0719570 B1 | 4/2003 |
| EP | 1308971 A2 | 5/2003 |
| EP | 1007140 B1 | 10/2003 |
| EP | 1372782 A2 | 1/2004 |
| EP | 0870517 B1 | 6/2004 |
| EP | 1061849 B1 | 11/2005 |
| EP | 1060762 B1 | 8/2006 |
| EP | 0836413 B1 | 8/2008 |
| WO | WO9104069 A1 | 4/1991 |
| WO | WO9638200 A1 | 12/1996 |
| WO | WO9712645 A1 | 4/1997 |
| WO | WO0054953 A1 | 9/2000 |
| WO | WO0137286 A1 | 5/2001 |
| WO | WO0180940 A1 | 11/2001 |
| WO | WO0186774 A1 | 11/2001 |
| WO | WO02056761 A2 | 7/2002 |
| WO | WO02065895 A2 | 8/2002 |
| WO | WO02072004 A2 | 9/2002 |
| WO | WO02089665 A1 | 11/2002 |
| WO | WO02092161 A1 | 11/2002 |
| WO | WO03013199 A2 | 2/2003 |
| WO | WO03037399 A2 | 5/2003 |
| WO | WO03059445 A2 | 7/2003 |
| WO | WO03061755 A2 | 7/2003 |
| WO | WO03063258 A1 | 7/2003 |
| WO | WO03063952 A2 | 8/2003 |
| WO | WO03063954 A1 | 8/2003 |
| WO | WO03063955 A1 | 8/2003 |
| WO | WO03063956 A2 | 8/2003 |
| WO | WO03063958 A1 | 8/2003 |
| WO | WO03063962 A1 | 8/2003 |
| WO | WO03070098 A2 | 8/2003 |
| WO | WO03073449 A1 | 9/2003 |
| WO | WO03073450 A1 | 9/2003 |
| WO | WO03086538 A1 | 10/2003 |
| WO | WO03090846 A2 | 11/2003 |
| WO | WO03090854 A1 | 11/2003 |
| WO | WO03095022 A2 | 11/2003 |
| WO | WO03063946 A2 | 4/2005 |
| WO | WO2006124481 A2 | 11/2006 |

OTHER PUBLICATIONS

File History for U.S. Appl. No. 11/015,807, filed Dec. 17, 2004

International Search Report and Written Opinion issued in PCT/US2009/059093, mailed Dec. 29, 2009.

International Search Report and Written Opinion issued in PCT/US2009/068314, mailed Mar. 25, 2009, 14 pages.

Kerr, Martha, "Shock Rate Cut 70% With ICDs Programmed to First Deliver Antitachycardia Pacing: Results of the PainFREE Rx II Trial," Medscape CRM News, May 21, 2003.

Luechinger, Roger et al., "In vivo heating of pacemaker leads during magnetic resonance imaging", European Heart Journal 2005;26:376-383.

Nyenhuis, John A. et al., "MRI and Implantable Medical Devices: Basic Interactions With an Emphasis on Heting", IEEE Transactions on Device and Materials Reliability, vol. 5, No. Sep. 2005, pp. 467-480.

Schueler, et al., "MRI Compatibility and Visibility Assessment of Implantable Medical Devices", Journal of Magnetic Resonance Imaging, 9:596-603 (1999).

Shellock FG, "Reference manual for magnetic resonance safety, implants, and devices", pp. 136-139, 2008 ed. Los Angeles; Biomedical Research Publishing Group; 2008.

Shellock, Frank G. et al., "Cardiovascular catheters and accessories: ex vivo testing of ferromagnetism, heating, and artifacts associated with MRI", Journal of Magnetic Resonance Imaging, Nov./Dec. 1998; 8:1338-1342.

Sweeney, Michael O. et al., Appropriate and Inappropriate Ventricular Therapies, Quality of Life, and Mortality Among Primary and Secondary Prevention Implantable Cardioverter Defibrillator Patients: Results From the Pacing Fast VT REduces Shock Therapies (PainFREE Rx II) Trial, American Heart Association, 2005.

Wilkoff, Bruce L. et al., "A Comparison of Empiric to Physician-Tailored Programming of Implantable Cardioverter-Defibrillators Results From the Prospective Randomized Multicenter EMPIRIC Trial," Journal of the American College of Cardiology vol. 48, No. 2, 2006. doi:10.1016/j.jacc.2006.03.037.

\* cited by examiner

MRI OPERATION MODES FOR IMPLANTABLE MEDICAL DEVICES

CROSS-REFERENCE TO RELATED APPLICATIONS

This application is a continuation of U.S. patent application Ser. No. 13/178,571, filed Jul. 8, 2011, now U.S. Pat. No. 8,543,207, which is a division of U.S. patent application Ser. No. 11/015,807, now U.S. Pat. No. 8,014,867, filed Dec. 17, 2004, all of which are hereby incorporated by reference in their entirety.

BACKGROUND OF THE INVENTION

The present invention relates generally to implantable medical devices ("IMDs"), and more particularly to systems, devices and methods for rendering IMDs more safe in the presence of strong electro-magnetic interference, such as those produced by a magnetic resonance imaging ("MRI") system.

IMDs can be used to provide a number of different medical therapies to patients. For example, therapeutic IMDs can include pacemakers, implantable cardioverter defibrillators ("ICDs"), blood pumps, drug delivery devices, neurostimulating devices, and the like. Some of the most common IMDs include pacemakers and ICDs (collectively referred to as cardiac rhythm management ("CRM") devices), which are used to control the heart rate when heart rhythm disorders occur.

Magnetic resonance imaging (MRI) is an efficient technique used in the diagnosis of many disorders, including neurological and cardiac abnormalities and other diseases. MRI has achieved prominence in both the research and clinical arenas. It provides a non-invasive method for examining internal body structures and functions. Because MRI has become such a useful diagnostic tool, it now is used extensively in hospitals and clinics around the world.

As one skilled in the art will appreciate, MRI systems produce extensive electromagnetic fields during operation. In particular, MRI systems generally produce (and utilize) three types of electromagnetic fields: 1) a strong static magnetic field; 2) a time-varying gradient field; and 3) a radio frequency (RF) field which consists of RF pulses used to produce an image. The static field produced by most MRI systems has a magnetic induction ranging from about 0.5 to about 1.5 T. The frequency of the RF field used for imaging is related to the magnitude of the static magnetic field, and, for current-generation MRI systems, the frequency of the RF field ranges from about 6.4 to about 64 MHz. The time-varying gradient field is used in MRI for spatial encoding, and typically has a frequency in the Kilohertz range.

These strong electromagnetic fields produced by MRI systems can cause problems for implantable medical devices, such as CRM devices. For example, the static magnetic field can affect the magnetically controlled (reed) switch that prevents inappropriate programming of a pulse generator ("PG"), and in some cases, it can saturate the core of inductive switching power supplies, causing difficulties for some implantable device power supplies. Further, the time-varying gradient field can generate significant voltage in CRM device leads, which can cause false cardiac event sensing. Finally, some tests have shown that the RF field produced in MRI systems can cause CRM device heating, and voltage generation in the CRM device circuitry and leads. Of particular concern are the MR-induced voltages, which potentially can inhibit pacing and/or ICD defibrillation, or which can induce excessively rapid pacing and/or inappropriate ICD defibrillation shocks. Both of these malfunctions can be life-threatening events. Indeed, some deaths have been reported for patients with implanted CRM systems who were inadvertently subjected to MRI scans. As a result, both the U.S. Food and Drug Administration (FDA) and many pacemaker manufacturers have issued warnings against pacemaker recipients undergoing MRIs.

Also, as one skilled in the art will appreciate, the adverse effects of MRI fields are not limited to CRM devices. MRI fields can adversely affect other IMDs, as well. Thus, a need exists for systems, methods, and/or devices that can mitigate the hazards associated with using CRM devices and other IMDs in an MRI environment.

BRIEF SUMMARY OF THE INVENTION

One embodiment of the present invention relates to an implantable medical device ("IMD") that can be programmed from one operational mode to another operational mode when in the presence of electro-magnetic interference ("EMI"). In accordance with this particular embodiment, the IMD includes a communication interface for receiving communication signals from an external device, such as a command to switch the IMD from a first operation mode to a second operation mode. The IMD further includes a processor in electrical communication with the communication interface, which is operable to switch or reprogram the IMD from the first operation mode to the second operation mode upon receiving a command to do so. In addition, the IMD includes a timer operable to measure a time period from when the processor switches the IMD to the second operation mode. In accordance with this aspect of the invention, the processor is in electrical communication with the timer, and is further operable to switch the IMD from the second operation mode back to the first operation mode when the measured time period reaches a predetermined time period. In one embodiment, the timer is separate from the processor, and in another embodiment, the processor can act as the timer.

In one embodiment, the IMD is a cardiac pacing device. Thus, in accordance with this embodiment, the first operation mode is a non-fixed-rate pacing mode, and the second operation mode is a fixed-rate pacing mode. In another embodiment, the first operation mode is can be a demand pacing mode, and the second operation mode can be a non-demand or asynchronous pacing mode In another embodiment, the IMD is an implantable cardioverter defibrillator. Thus, in accordance with this embodiment, the first operation mode is a mode in which tachy therapy is enabled, and the second operation mode is a mode in which tachy therapy is disabled.

In one embodiment, the IMD is switched from the first operation mode to the second operation mode prior to a patient receiving a magnetic resonance imaging (MRI) scan, and the predetermined time period is set so that the implantable medical device is switched back to the first operation mode after the MRI scan is complete.

In accordance with another embodiment, the present invention is a cardiac rhythm management (CRM) device, which comprises a processor for executing computer program instructions, and a communication interface operable to receive communication signals from an external device and transmit the communication signals to the processor. The communication signals can include commands to switch or reprogram the CRM device between an MRI mode and a non-MRI mode. In one embodiment, the MRI mode can be a CRM device mode that allows the CRM device to switch from a normal operation mode to an MRI-safe operation mode in the presence of one or more MRI electromagnetic fields. Further, the non-MRI mode can be a CRM device mode that prohibits the CRM device from switching from the normal operation mode to the MRI-safe operation mode.

In accordance with this particular embodiment of the invention, the CRM device further comprises an electromagnetic field sensor, which is operable to measure electromagnetic fields generated by an MRI system and communicate the electromagnetic field measurements to the processor. In this embodiment, the CRM device is operable to configure itself in an MRI mode upon receiving a command from the external device to do so. Then, using the electromagnetic field sensor, the CRM device can determine whether the measured MRI electromagnetic fields are above or below a predetermined field strength threshold. If the MRI electromagnetic fields are above the predetermined threshold, the CRM device is operable to switch from its normal operation mode to an MRI-safe operation mode. The CRM device then will stay in the MRI-safe operation mode until the MRI electromagnetic fields drop below the predetermined level, at which time, the CRM device then will switch back to its normal operation mode. Finally, in accordance with this particular embodiment, the CRM device will switch out of the MRI mode upon receiving a command from an external device to do so.

In one embodiment, the CRM device is a cardiac pacing device. In this embodiment, the normal operation mode is a non-fixed-rate pacing mode, and the MRI-safe operation mode is a fixed-rate pacing mode. Further, in another embodiment, the CRM device is an implantable cardioverter defibrillator. Thus, in this embodiment, the normal operation mode is a mode in which tachy detection is enabled, and the MRI-safe operation mode is a mode in which tachy detection is disabled.

In other embodiments, the present invention relates to methods performed by the aforementioned devices. In still other embodiments, the present invention relates to other devices and methods for programming the devices into safe modes of operation as discussed in more detail below and as set forth in the claims.

A more complete understanding of the present invention may be derived by referring to the detailed description of preferred embodiments and claims when considered in connection with the figures.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION OF THE INVENTION

Figure 1:
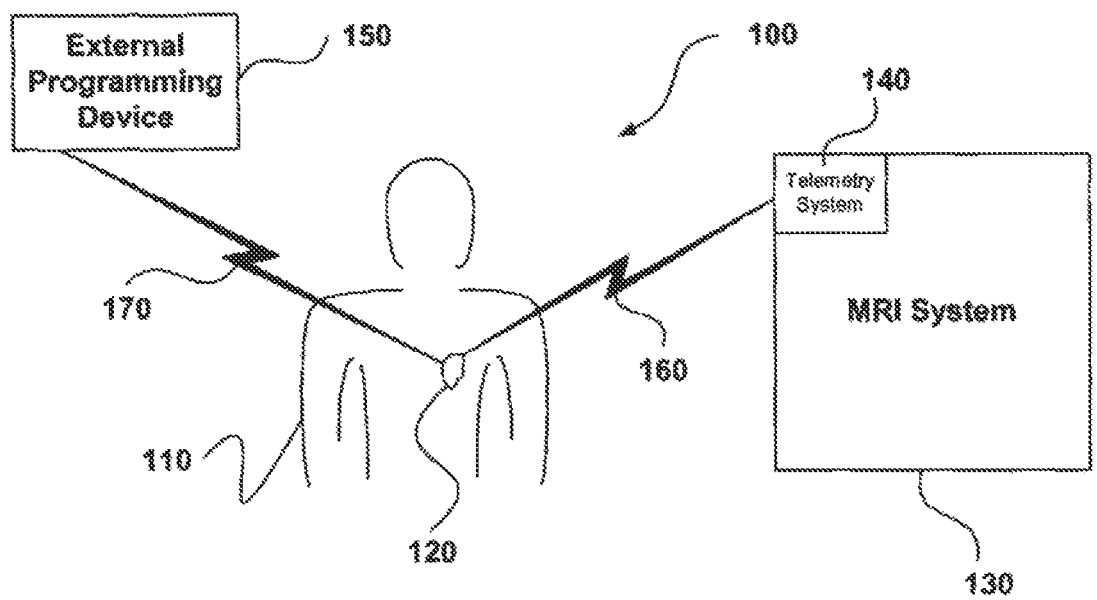
FIG. 1 is a diagram showing the relationship between an implantable medical device and an MRI system in accordance with one embodiment of the present invention.

The present invention relates generally to implantable medical devices ("IMDs"), and more particularly to systems, devices and methods for rendering IMDs more safe in the presence of strong electro-magnetic interference ("EMI"), such as those produced by magnetic resonance imaging ("MRI") systems. In accordance with at least some embodiments, the present invention relates to IMDs that can be programmed to alter their operational modes in the presence of electro-magnetic interference to prevent damage to the IMD and/or the patient. As discussed in more detail below, the IMDs can be programmed from an external programming device, or the IMDs can be configured to automatically change operational modes in the presence of the EMI.

As used herein, the term electro-magnetic interference ("EMI") can refer to any EMI, such as static magnetic fields, gradient magnetic fields, and/or radio frequency ("RF") fields generated by an MRI system, or any other electro-magnetic fields or interference that can be generated by any number of different sources, such as metal detectors, radio transmitters, cellular phones, microwave generators, electronic article surveillance systems, etc. Thus, the present invention can be used to render IMDs more safe in the presence of any EMI and is not limited to any particular EMI environment. As one skilled in the art will appreciate, however, operating IMDs during MRI scans or at least recognizing the presence of the IMDs prior to an MRI scan is of particular interest to health care providers. Thus, for this reason, and for ease of presentation, the present invention will be discussed with reference to MRI systems. The present invention, however, is not limited to an MRI environment.

Also, as discussed above, some embodiments of the invention relate to switching operational modes of the IMDs to render them more safe in the presence of EMI, and in particular, MRI fields. In these embodiments, the IMDs are switched from a "normal" operational mode to an "MRI-safe" operation mode. As one skilled in the art will appreciate, a normal operational mode is the operational mode of the IMD prior to it being altered in presence of EMI. Thus, for cardiac rhythm management devices ("CRM"), such as Brady and/or Tachy devices, for example, the normal operational mode is the CRM's initially programmed mode.

The term "MRI-safe" mode, as used herein, can refer to any operational mode of an IMD that is a safe operational mode in the presence of EMI. For example, for a Brady device (as well as a Brady engine in a Tacky device) an MRI-safe mode might be a fixed-rate and/or non-demand (or asynchronous) pacing mode as opposed to a rate-responsive and/or demand pacing mode. In some embodiments, an MRI-safe mode can be both a non-demand mode (i.e., VOO) and a non-rete-responsive mode. Thus, in accordance with one embodiment, switching a Brady device to an MRI-safe mode might entail switching the Brady engine to a VOO, AOO or DOO pacing mode. The mode to which the device is switched will depend, of course, on the original programmed mode of the device. In one embodiment, a device, which is normally programmed to a Dxx mode (i.e., DDDR, DDD, DDI, or DVI) would switch to DOO when in MRI-safe mode. Similarly, a device programmed to Vxx mode would switch to VOO, and a device programmed to Axx mode would switch to AOO mode.

Further, in other embodiments, an MRI-safe mode for a Tacky device might comprise turning-off tacky detection and/or therapy, as well as switching the Brady engine of the Tacky device to a fixed-rate, non-demand pacing mode. In these embodiments, turning the tacky detection off will ensure that noise that might be induced on the device leads by an MRI scan is not mistaken by the device for tachycardia, which might result in an inappropriate shock during an MRI. Also, for CRM devices, there may be other modes of operation that are considered safe in an MRI environment, so the present invention is not limited to the MRI-safe modes discussed herein. Further, as one skilled in the art will appreciate, other types of IMDs will have different mode types that might be considered safe in an MRI environment, and those modes also are considered MRI-safe modes for purposes of the present invention.

Referring now to FIG. 1, diagram 100 illustrates an MRI system environment in which it can be beneficial to detect the presence of an IMD and alter the processing of the MRI system and/or the IMD to prevent damage to the IMD and/or the patient with the IMD. This particular diagram illustrates a patient 110 having an IMD 120 in the presence of an MRI system 130. In this particular embodiment, MRI system 130 includes a telemetry system 140, which is operable to communicate wirelessly (e.g., wireless link 160) with IMDs. Telemetry system 140 can be integral with MRI system 130, or telemetry system 140 can be a separate device in communication with MRI system 130, for example, via a USB connection, a firewire connection, a network, or any other suitable communication connection. In addition, as illustrated in diagram 100, IMD 120 further is operable to wirelessly communicate (e.g., wireless connection 170) with an external programming device 150, which can collect information from IMD 120, as well as reprogram IMD 120.

Thus, as discussed in more detail below, in some embodiments, MRI system 130 can detect the presence of an IMD 120 (e.g., using telemetry system 140), and then prevent MRI scans if the IMD is not in a safe mode of operation. In other embodiments, IMD 120 can be operable to detect the presence of EMI (for example magnetic and/or RF signal from MRI system 130) and then alter its programming (either automatically, or manually via external programming device 150) to put the IMD in a safe mode of operation. In still other embodiments, IMD 120 can be operable to detect the presence of MRI system 130, and then send commands or information to MRI system 130, disabling MRI scans until the IMD can be programmed into a safe mode of operation. In still other embodiments, IMD 120 can be manually programmed (e.g. via external programming device 150) into safe modes of operation prior to being exposed to EMI, such as MRI scans, or the like. The inter-working relationships between IMD 120 and MRI system 130, telemetry system 140 and external programming device 150 will be discussed in more detail below.

In accordance with the present invention, IMD 120 can be any type of implantable medical device that might be affected by EMI, and in particular, MRI scans. For example, IMD 120 can be a pacemaker, an implantable cardioverter defibrillator ("ICD"), a cardiac resynchronization device, a bi-ventricular pacer, a ventricular assist blood pump, a drug delivery pump, a drug infusion device, a neurostimulating device, an intra-ocular shunt, an intra-cranial shunt, or any other suitable implantable device that might be sensitive to EMI. In the embodiment illustrated in FIG. 1, IMD 120 is a cardiac device, such as a pacemaker, an ICD, or the like.

Figure 2:
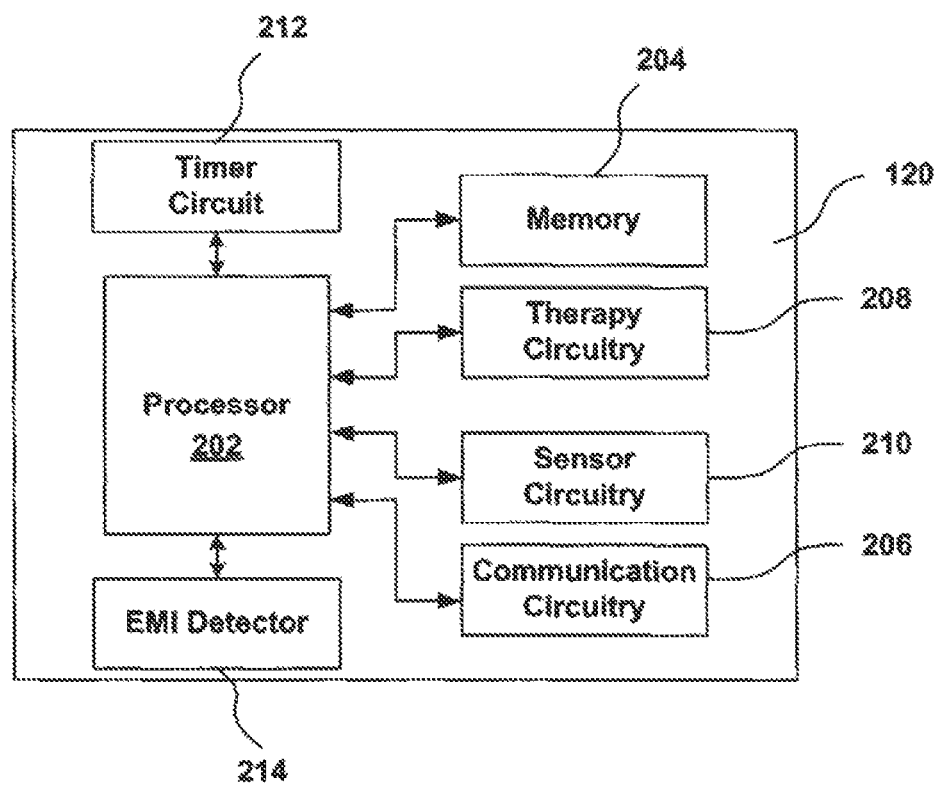
FIG. 2 is a block diagram of one embodiment of an implantable medical device that can be used in the present invention.

Referring now to FIG. 2, one embodiment of an IMD 120 is illustrated. In accordance with the illustrated embodiment, IMD 120 comprises a processor 202, a memory 204, communication circuitry 206, therapy circuitry 208 and sensor circuitry 210, timer circuitry 212, and an EMI detector 214. In this particular embodiment, memory 204, communication circuitry 206, therapy circuitry 208, sensor circuitry 210, timer circuitry 212, and EMI detector 214 all are in electrical communication with processor 202, as is illustrated by the arrows in FIG. 2.

The embodiment of IMD 120 illustrated in FIG. 2 is merely one exemplary embodiment of an IMD. One skilled in the art will appreciate that other IMDs might include more features or functionality not shown in FIG. 2, or other IMDs might include less features and/or functionality. For example, some IMDs might not provide therapy, so therapy circuitry 208 might not be present. Further, as discussed below, having both timer circuitry 212 and EMI 214 might not be needed in all embodiments, so IMD 120 may be configured without one or both of those features. Thus, the present invention is not limited to the IMD illustrated in FIG. 2.

As one skilled in the art will appreciate, processors and memory devices are well known in the art, and the specific type and/or style of processor or memory device that can be used in IMD 120 is not limited. Accordingly, processor 202 can be any suitable processing device currently known or hereinafter developed, and memory device 204 can be any suitable memory device currently known or hereinafter developed.

Communication circuitry 206 is circuitry that allows IMD 120 to communicate with other devices, such as external programming device 160, telemetry system 140, other IMDs, or other external devices. As discussed above, IMD 120 can communicate with other devices via a wireless connection. The wireless connection can be, for example, a near field radio frequency (RF) communication connection, a far field RF communication connection, an acoustic communication connection (e.g., an ultrasound connection), an optical communication connection, or any other suitable wireless communication connection.

In one embodiment, communication circuitry 206 can include circuitry for both near field RF telemetry and far field RF telemetry. For example, various embodiments of communication circuitry that can be used in IMD 120 are disclosed in Published U.S. Patent App. No. US 2003/0114897 A1, published on Jun. 19, 2003, and entitled "Implantable Medical Device with Two or More Telemetry Systems," and Published U.S. Patent App. No. U.S. 2003/0114898 A1, published on Jun. 19, 2003, and entitled "Telemetry Duty Cycle Management System for an Implantable Medical Device," both of which are incorporated by reference herein for all purposes.

In addition, in other embodiments, power saving wireless communication circuitry and methods can be used. For example, the IMD communication circuitry 206 can be configured to reside in a power-saving, sleep mode for a majority of the time. In accordance with this embodiment, communication circuitry 206 can be configured to "wake-up" on a periodic basis to communicate with an external device. Upon "wake-up" the external device will monitor for RF activity, and if the external device locates it, communication between the IMD and the external device can be initiated. There are a number of different ways IMD power-saving modes can be implemented, and the present invention is not limited to any particular one. Indeed, the aforementioned Published U.S. Patent App. Nos. US 2003/0114897 A1 and US 2003/0114898 A1 disclose different ways of implementing IMD power-saving modes, which, as discussed above, are incorporated herein by reference for all purposes. In addition, additional power management systems and methods are disclosed in Published U.S. Patent App. No. US 2003/0149459 A1, published on Aug. 7, 2003, and entitled "Methods and Apparatuses for Implantable Medical Device Telemetry Power Management" and Published U.S. Patent App. No. US 2002/0147388 A1, published on Oct. 10, 2002, and entitled "Passive Telemetry for Implantable Medical Device," both of which are incorporated by reference herein for all purposes.

Further, in accordance with other embodiments, communication circuitry 206 can be configured to communicate with an intermediary telemetry device, which, in turn, can facilitate communication with the external monitoring device 104 and/or external computing device 106. One example of this type of configuration is disclosed in Published U.S. Patent App. No. US 2003/0130708, published on Jul. 10, 2003, and entitled "Two-Hop Telemetry Interface for Medical Device," the entirety of which is incorporated by reference herein for all purposes. In addition, other configurations for RF telemetry are known, and communication circuitry 206 can embody those configurations, as well. Thus, as one skilled in the art will appreciate, communication circuitry 206 is not limited by any particular configuration or communication means.

Therapy circuitry 208 comprises circuitry for providing one or more therapeutic functions to a patient. For example, therapy circuitry 208 can include circuitry for providing heart pacing therapy, cardiac defibrillation therapy, cardiac resynchronization therapy, drug delivery therapy, or any other therapy associated with a suitable IMD. In the case of cardiac therapy (e.g., pacing, defibrillation, etc.), therapy circuitry 208 can include cardiac leads for delivering the therapy to particular locations in the heart. In other embodiments, the therapy circuitry and/or therapy delivery mechanisms can reside in a satellite device wirelessly coupled to the IMD body 120, as discussed below.

Sensor circuitry 210 comprises the sensors and circuitry needed to obtain or measure one or more physiologic parameters. For example, to obtain a blood pressure (e.g., intravascular or intracardiac blood pressure), sensor circuitry 210 comprises one or more pressure sensors and associated circuitry for recording the pressure accurately. Pressure sensors and the associated circuitry are well known in the art, and therefore, will not be disclosed in detail herein. In addition, in other embodiments, sensor circuitry 210 can be configured to obtain other physiologic parameters, such as temperature, electrical impedance, position, strain, pH, fluid flow, blood oxygen levels, and the like. In these cases, sensor circuitry 210 will include suitable bio-sensors for obtaining the corresponding physiologic parameters. Also, as one skilled in the art will appreciate, the sensors and/or sensor circuitry can be, and many times are, electrically coupled to IMD 120, but placed remotely from the IMD; e.g., at the end of a lead or in a satellite device in wireless communication with IMD 120.

In an alternative embodiment, IMD 120 can comprise a planet/satellite configuration, in which the satellite portion of the IMD includes sensor and/or therapy delivery circuits and mechanisms. Such a configuration is disclosed in Published U.S. Patent Application No. US 2003/0158584 A1, published on Aug. 21, 2003, and entitled "Chronically-Implanted Device for Sensing and Therapy," the entirety of which is incorporated herein by reference for all purposes. In this system, the planet or main body of the IMD communicates with one or more satellite sensor/therapy devices either by an electrical wire connection or wirelessly. In some embodiments, the planet or main body can command each satellite to provide sensing functions and therapy functions, such as delivering cardiac electrical pulses, drug delivery, or other functions, as discussed above. In other embodiments, the satellite devices can function autonomously, and then communicate with the planet device at their own direction, at the planet's direction, or at timed intervals. The relationships between the planet device and the satellite device(s) are discussed in more detail in the incorporated reference.

Timer circuitry 212 can comprise any suitable circuitry and/or functionality for tracking time periods. Timer circuitry can be a separate timer circuit, as illustrated in FIG. 2, or the timing functionality can be performed, for example, by processor 202. As one skilled in the art will appreciate, timers are well known in the art, and the particular circuitry that performs the timing functionality is not important. Thus, the present invention is not limited to any particular timer embodiment. The use of a timer and/or timer circuitry 212 will be discussed in greater detail below.

Finally, EMI detector 214 can comprise one or more detectors for detecting electro-magnetic fields and/or radiation. For example, EMI detector 214 can include a sensor for detecting the presence and/or strength of magnetic fields, such as a Hall-effect sensor, or other suitable magnetic field detectors currently known or hereinafter developed. In addition, EMI detector 214 can further include sensors for detecting the presence of high-frequency radiation that can be produced by MRI systems, radar, radio transmitters, and the like. Again, the purpose and use of EMI detector 214 will be discussed in greater detail below.

Figure 3:
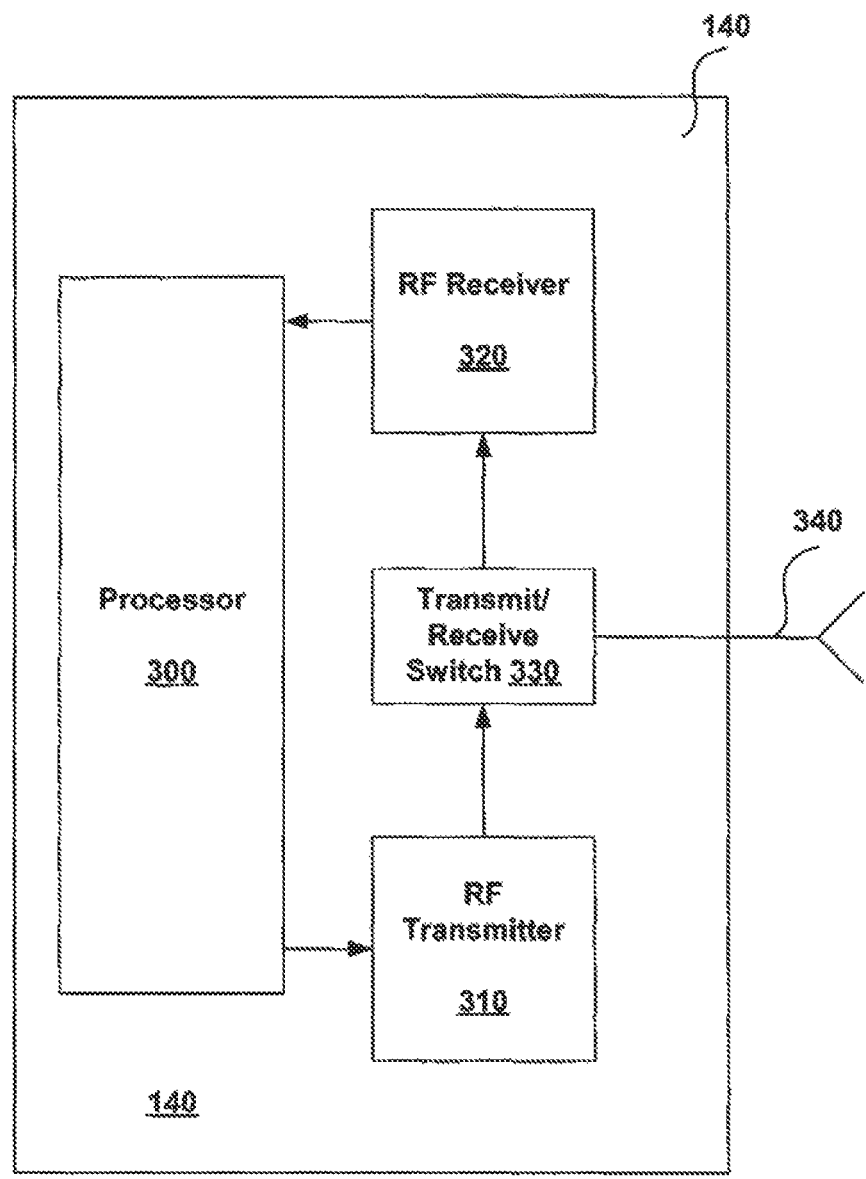
FIG. 3 is a block diagram of one embodiment of a telemetry system that can be used in the present invention.

Referring now to FIG. 3, one embodiment of a telemetry system 140 that can be associated with MRI system 130 is shown. As discussed above, telemetry system 140 is operable to communicate with IMDs that might be near MRI system 130. In the illustrated embodiment, telemetry system 140 comprises a processor 300, an RF transmitter 310, and RF receiver 320, a transmit/receive ("T/R") switch 330 and an antenna 340. In this particular embodiment, processor 300 is interfaced to RF transmitter 310 and RF receiver 320, both of which are connected to antenna 340. T/R switch 330 passes RF signals uni-directionally from transmitter 310 to antenna 340 and from antenna 340 to the receiver 320. To communicate data to an IMD, processor 300 sends data to transmitter 310, which generates an RF carrier signal for a specified time period that is emitted from the antenna 340. As one skilled in the art will appreciate, the carrier signal includes the data to be transmitted to the IMD. The transmitted carrier signal then reaches the IMD, which, in turn, receives and processes the data. Similarly, when communicating data or information from the IMD to telemetry circuitry 140, the communication circuitry 206 of the IMD is operable to generate and transmit an RF carrier signal to antenna 340. After reaching antenna 340, the carrier signal is conveyed through T/R switch 330 to receiver 320, where the signal is demodulated to extract the digital message data. The digital data may then be processed and interpreted by software executed by the processor 300.

T/R switch 330 of the telemetry circuitry enables receiver 320 to receive signals without having to recover from saturation from signals that were previously emitted by antenna 340 that originate from transmitter 310. As an alternative to the T/R switch, a directional coupler could be used to separate the transmit and receive signals, or separate antennas with orthogonal linear polarization states can be provided for the transmitter and receiver, thus enabling simultaneous radiation of the carrier signal by the transmitter antenna and reception of the reflected carrier by the receiver antenna.

A more complete description of near-field and far-field telemetry is set forth in the patents incorporated by reference above. As one skilled in the art will appreciate, the present invention is not limited to any specific telemetry circuitry or functionality.

Referring again to FIG. 1, external programming device 150 can be any suitable computing device adapted to communicate with IMD 120 and/or telemetry circuitry 140 and process data from those devices. For example, in the case of a cardiac rhythm management ("CRM") IMD (e.g., pacemaker, ICD, etc.), external programming device 150 might be a programmer used by physicians, specialists, or other health care providers to extract data from and program cardiac IMDs. Programmers are well known in the art. In addition, in other embodiments, external programming device 150 can be a repeater device associate with a patient. Examples of one or more repeater-type devices are disclosed in U.S. Pat. No. 6,607,485, issued on Aug. 9, 2003, and entitled "Computer Readable Storage Medium Containing Code for Automated Collection and Analysis of Patient Information Retrieved from an Implantable Medical Device for Remote Patient Care," the entirety of which is incorporated by reference herein for all purposes.

Figure 4:
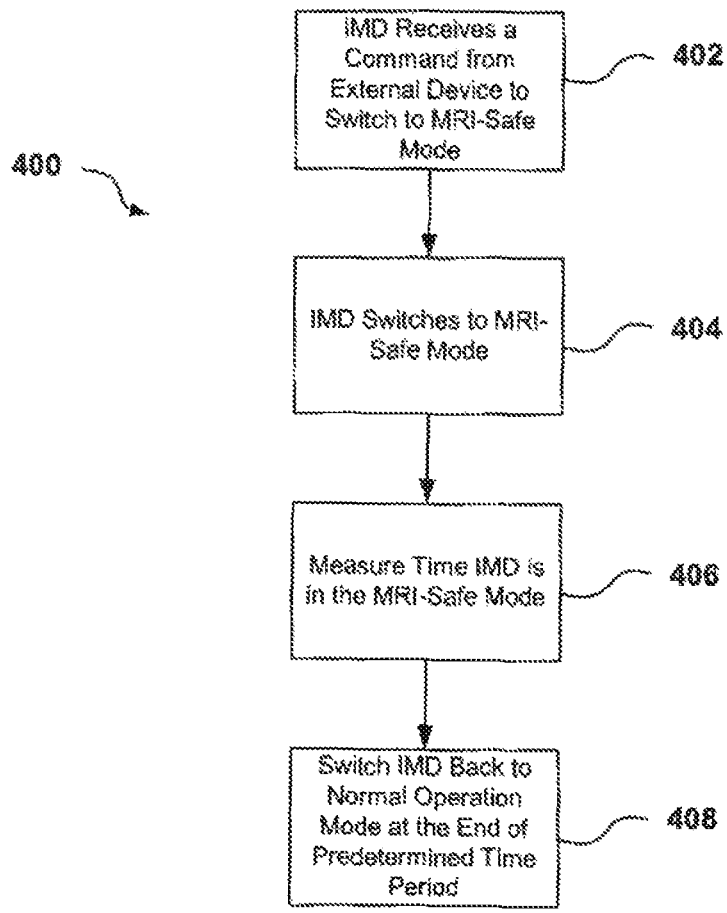
FIGS. 4-10 are flow charts illustrating different embodiments of methods of the present invention.

Referring now to FIG. 4, flow chart 400 illustrates one embodiment of a method for programming an IMD in a safe mode of operation while in the presence of MRI systems or other EMI. In accordance with the method illustrated in flow chart 400, an IMD (e.g., IMD 120 in FIG. 1) receives a command from an external programming device to switch to a safe mode of operation (e.g., an MRI-safe mode as discussed above) (block 402). The external programming device could be external programming device 150, or the external programming device could be associated with MRI system 130 and could communicate with the IMD via a telemetry interface, such as telemetry system 140.

Upon receiving a command to switch to a safe mode of operation, a processor within the IMD (e.g., processor 202 of IMD 120) will program the IMD's operational mode to safe mode (block 404), and then a timer within the IMD (e.g., timer 212 of IMD 120) will begin measuring a time period from when the reprogram occurs (block 406). When the MRI or other EMI exposure is complete, the IMD can be manually programmed back to a normal mode of operation by sending it a command to do so. In accordance with this particular embodiment, the purpose of the timer is to ensure that the IMD does not remain in the safe mode of operation for extended periods of time (e.g., should the operator forget to send the manual command to return the device to normal mode), because generally, it is in the patient's best interest to have the IMD operating in its normal mode of operation as originally programmed. The IMD's safe mode of operation should be limited to time periods when the IMD is in the presence of EMI, such as MRI scans, and the like. Thus, after the timer reaches a predetermined time (e.g., a time period after an MRI scan is complete), if the IMD has not received a command to switch back to normal mode of operation, the IMD is switched back from the safe mode of operation to its normal mode of operation (block 408). As discussed above, the processor within the IMD can be operable to reprogram the IMD's operation mode switch.

Figure 5:
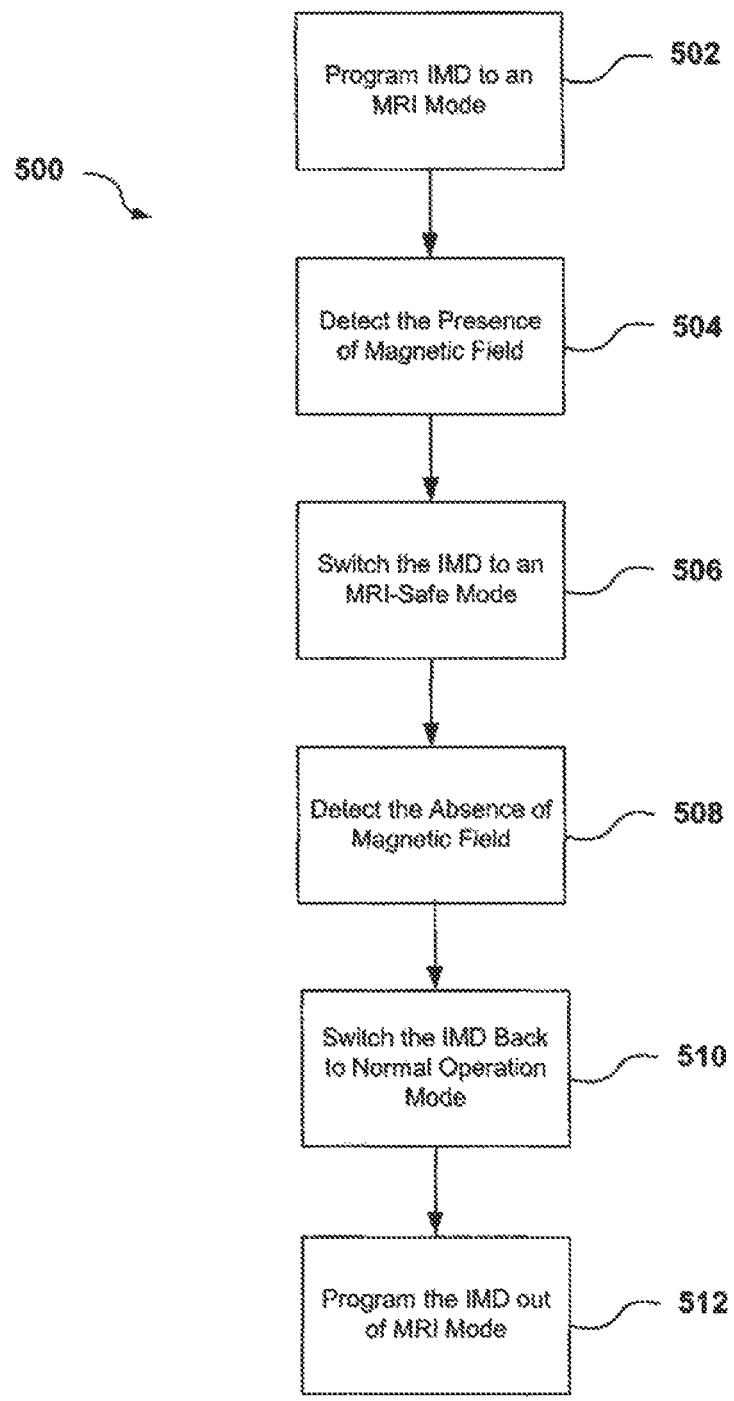

Referring now to FIG. 5, flow chart 500 illustrates another embodiment of a method for programming an IMD in a safe mode of operation while in the presence of MRI systems or other EMI. In accordance with the method illustrated in flow chart 500, an IMD (e.g., IMD 120 in FIG. 1) receives a command from an external programming device to reprogram to an MRI-mode of operation (block 502). The external programming device could be external programming device 150, or the external programming device could be associated with MRI system 130 and could communicate with the IMD via a telemetry interface, such as telemetry system 140.

In accordance with this particular embodiment of the invention, the MRI-mode of operation is not a "safe mode" in which a Brady device is set to a fixed-rate, non-demand pacing mode or tacky detection or therapy of a tacky device is disabled, as discussed above. In accordance with this particular embodiment, the MRI-mode of operation is a pre-MRI scan setting in which a magnetic field detector is activated (e.g., EMI detector 214 of IMD 120 in FIG. 2). Thus, when the magnetic field detector of the IMD detects a magnetic field of sufficient strength (i.e., in the presence of an MRI system) (block 504), the IMD will automatically switch to a safe mode of operation (block 506), as defined above. Once in safe mode, the magnetic field detector of the IMD will continue to monitor for the presence and/or absence of the magnetic field (block 508). When the magnet field has dissipated to safe level, the IMD will automatically switch back to its normal mode of operation (block 510).

Further, as one skilled in the art will appreciate, it can be unsafe to have an IMD operating in the MRI-mode of operation for long periods of time, because the IMD will automatically switch to a safe mode in the presence of magnetic fields, even when it is not necessary or desirable to have the IMD in the safe mode. Thus, in accordance with this particular embodiment, after an MRI scan is complete or after the IMD is positioned a safe distance from strong EMI, the IMD can be taken out of the MRI-mode of operation by receiving a command from an external programming device and processing the command (block 512).

Figure 6:
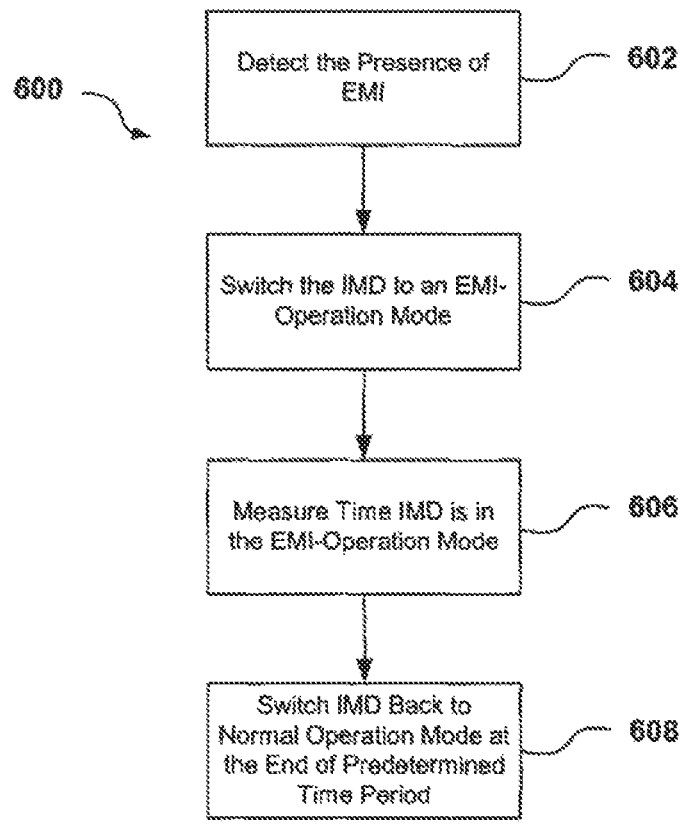

Referring now to FIG. 6, flow chart 600 illustrates an embodiment of a method for operating an IMD in a safe mode of operation while in the presence of EMI. In accordance with the method illustrated in flow chart 600, an IMD (e.g., IMD 120 in FIG. 1) includes an EMI detector (EMI detector 214 in FIG. 2), which is operable to detect EMI, such as magnetic fields and/or RF energy (block 602). Thus, when the magnetic field detector of the IMD detects a magnetic field of sufficient strength (e.g., in the presence of an MRI system), the IMD will automatically switch to a safe mode of operation, as defined above (block 604), and then a timer within the IMD (e.g., timer 212 of IMD 120) will begin measuring a time period from when the switch to safe mode occurs (block 606). As discussed above, the purpose of the timer is to ensure that the IMD does not remain in the safe mode of operation for extended periods of time. Thus, after the timer reaches a predetermined time (e.g., a time period after the IMD is a safe distance from the EMI), the IMD is switched back from the safe mode of operation to its normal mode of operation (block 608). As discussed above, the processor within the IMD can be operable to reprogram the IMD's operation mode switches.

Figure 7B:
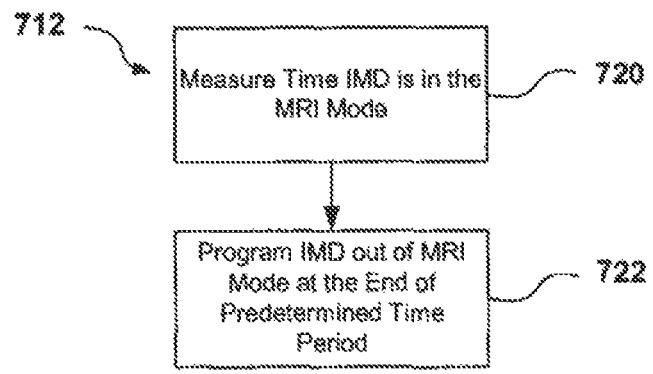
Figure 7A:
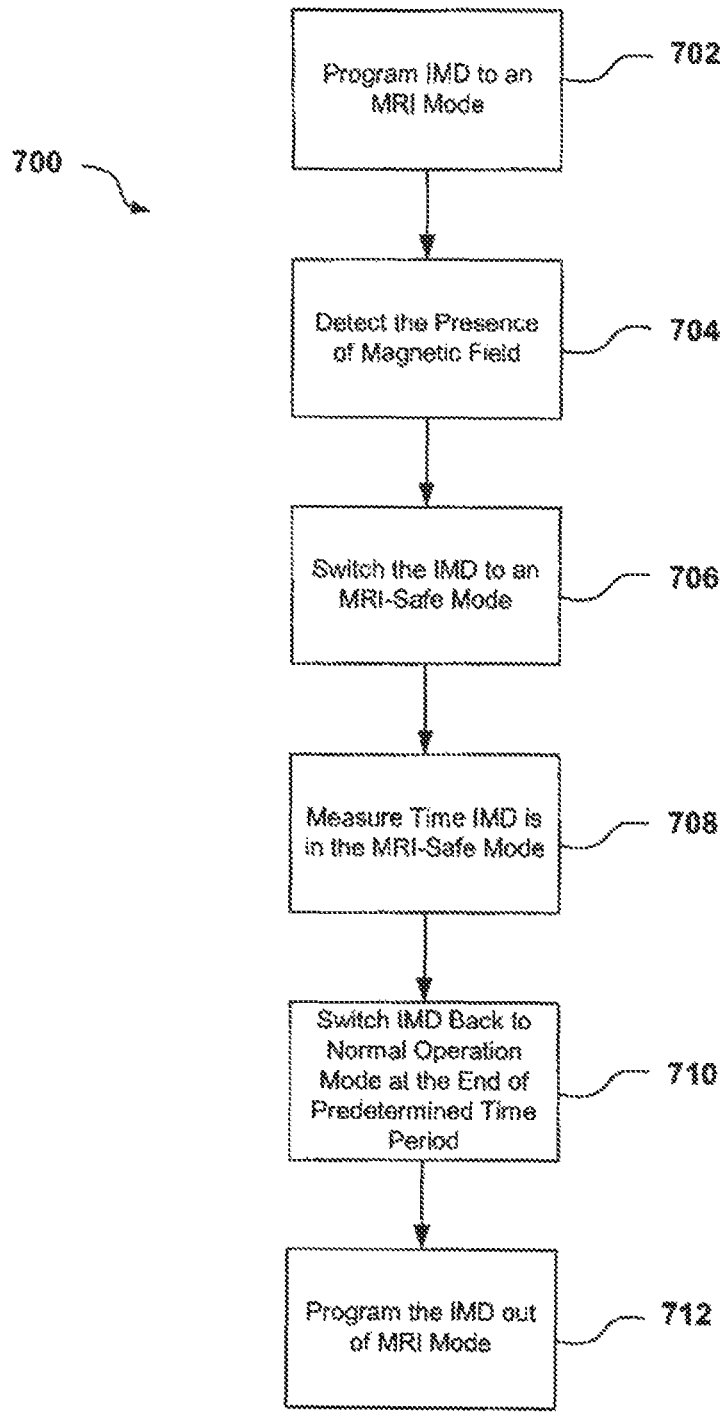

Referring now to FIG. 7a, flow chart 700 illustrates another embodiment of a method for programming an IMD in a safe mode of operation while in the presence of MRI systems or other EMI. In accordance with the method illustrated in flow chart 700, an IMD (e.g., IMD 120 in FIG. 1) receives a command from an external programming device to switch to an MRI-mode of operation, which is discussed above (block 702). The external programming device could be external programming device 150, or the external programming device could be associated with MRI system 130 and could communicate with the IMD via a telemetry interface, such as telemetry system 140.

As discussed above, the MRI-mode of operation is a pre-MRI scan setting in which a magnetic field detector is activated (e.g., EMI detector 214 of IMD 120 in FIG. 2). Thus, when the magnetic field detector of the IMD detects a magnetic field of sufficient strength (i.e., in the presence of an MRI system) (block 704), the IMD will automatically switch to a safe mode of operation (block 706), as defined above. Once in safe mode, a timer within the IMD (e.g., timer 212 of IMD 120) will begin measuring a time period from when the switch to safe mode occurs (block 708). As discussed above, the purpose of the timer is to ensure that the IMD does not remain in the safe mode of operation for extended periods of time. Thus, after the timer reaches a predetermined time (e.g., a time period after an MRI scan is has completed), the IMD is switched back from the safe mode of operation to its normal mode of operation (block 710).

After an MRI scan is complete or after the IMD is positioned a safe distance from strong EMI, the IMD can be taken out of the MRI-mode of operation (block 712). In one embodiment, the IMD can be taken out of the MRI-mode of operation by receiving a command from an external programming device and processing the command, as discussed above with reference to FIG. 5. In an alternative embodiment illustrated in FIG. 7b, instead of using an external programming device to switch the IMD out of MRI-mode, a timer can be used. In this particular embodiment, after the IMD is switched back to normal operation mode (block 710), a timer within the IMD (e.g., timer 212 of IMD 120) will begin measuring a time period from when the switch to normal mode occurs (block 720). Then, after the timer reaches a predetermined time, the IMD automatically is switched out of the MRI-mode of operation (block 722), so that it will not accidentally detect EMI and switch into safe mode again.

Figure 8:
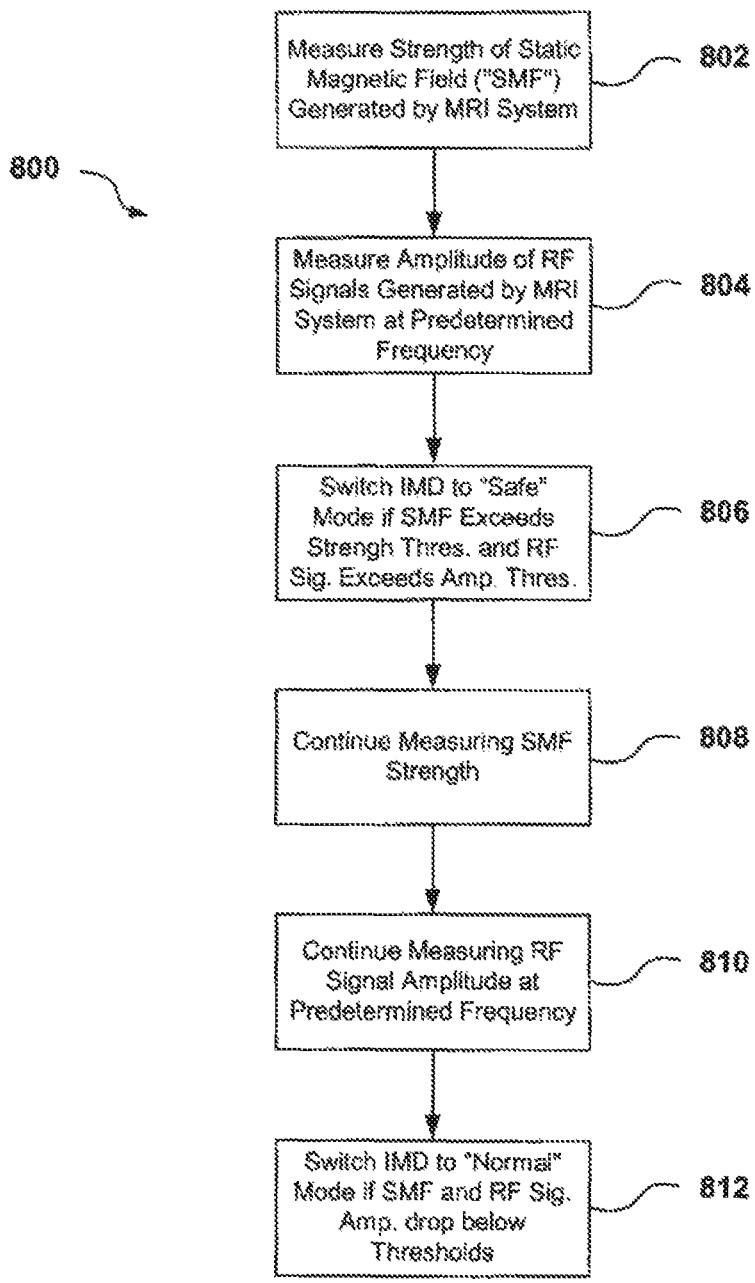

Referring now to FIG. 8, flow chart 800 illustrates yet another embodiment of a method of operating an IMD in a safe mode of operation while in the presence of MRI systems or other EMI. In accordance with the method illustrated in flow chart 800, an IMD (e.g., IMD 120 in FIG. 1) is operable to measure one or more electromagnetic field components generated by an MRI system, such as the strength of a static magnetic field (block 802), and/or the amplitude of RF signals at a predetermined frequency (block 804). In accordance with this aspect of the invention, the IMD can comprise one or more detectors for detecting the static magnetic field and/or the RF amplitude. In one embodiment, a single EMI detector (e.g., EMI detector 214 in FIG. 1) can be used to measure both the magnetic field and/or the RF amplitude. In an alternative embodiment, a hall effect sensor can be used to measure the magnetic field, and an RF sensor or detector can be used to measure the amplitude of the RF signals. As one skilled in the art will appreciate, a band pass or notch filter can be used to select the frequency at which the amplitude of the RF signal is measured. In one embodiment, the RF signal amplitude can be measured at about 64 MHz. In other embodiments, the RF signal can be measured at other frequencies.

In one embodiment, measuring the magnetic field and the RF amplitude can provide redundant measurements, so that an IMD will not switch to safe mode unless both conditions are met (if both conditions are met, the IMD most likely is near an MRI system). Thus, if the magnetic field exceeds a predetermined strength threshold (e.g., about 0.001 Tesla, or so), and/or the RF signal exceeds an amplitude threshold (e.g., about 0.2 mT per meter) at the particular frequency, the IMD automatically will switch to a safe mode of operation, as defined above (step 806). Once in safe mode, the IMD will continue to monitor the magnetic field and/or the RF signal amplitude at the predetermined frequency (blocks 808 and 810). When the magnetic field has dissipated to a safe level (e.g., below 0.001 T or less than 1% of the full field strength) and/or the RF signal amplitude drops, the IMD will automatically switch back to its normal mode of operation (block 812). While this particular embodiment uses both the static magnetic field strength and RF amplitude measurements, one skilled in the art will appreciate that other embodiments might only measure and use one of the measurements, or other electromagnetic field components can be used. Thus, the present invention is not limited to any one particular embodiment.

Figure 9:
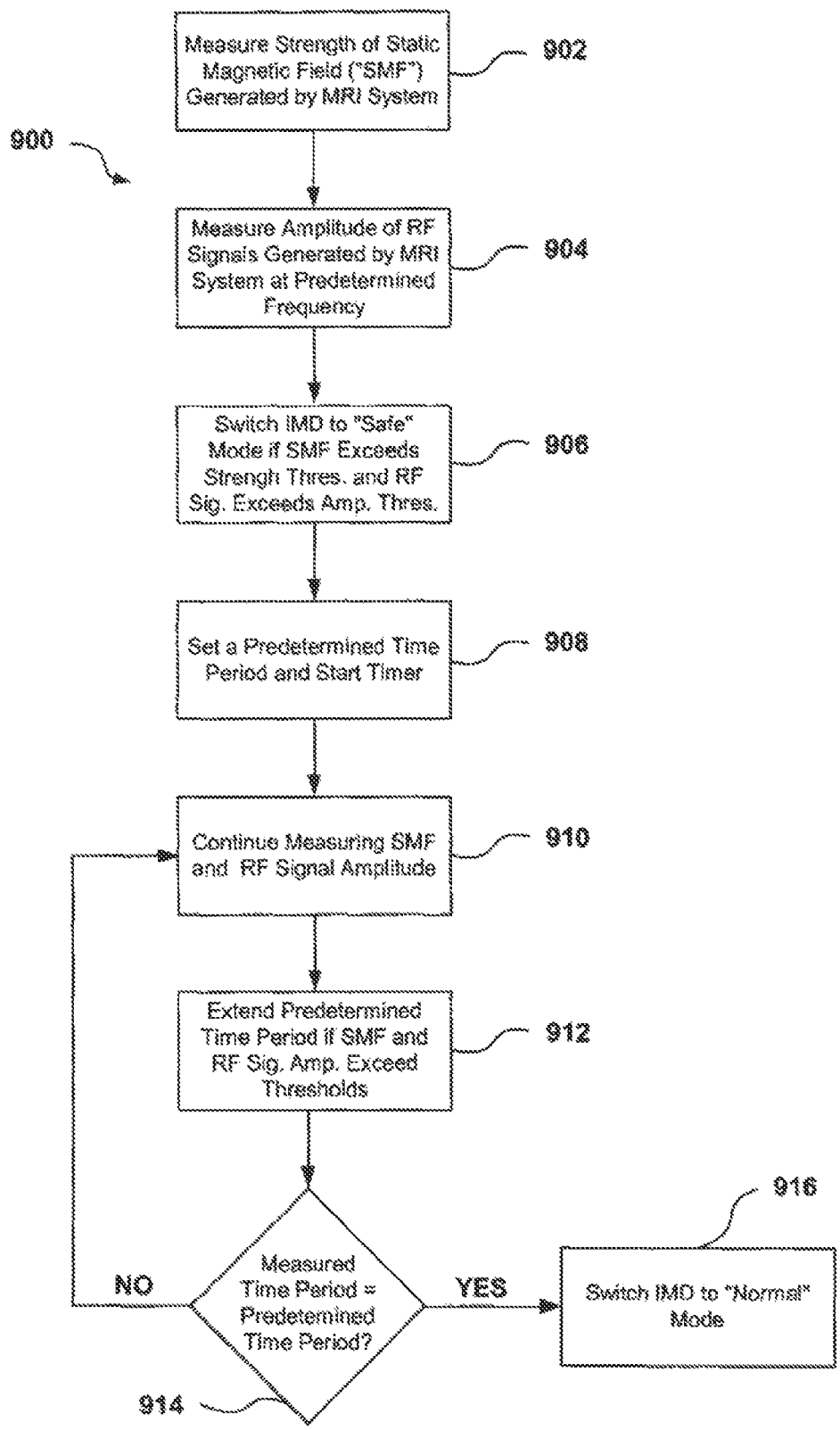

Referring now to FIG. 9, flow chart 900 illustrates yet another embodiment of a method of operating an IMD in a safe mode of operation while in the presence of MRI systems or other EMI. In accordance with the method illustrated in flow chart 900, an IMD is operable to measure the strength of a static magnetic field generated by an MRI system (block 902). In addition, the IMD is operable to measure the amplitude of RF signals generated by the MRI system at a predetermined frequency (block 904). These steps are similar to steps discussed above with reference to FIG. 8. Again, if the magnetic field exceeds a predetermined strength threshold, and the RF signal exceeds an amplitude threshold at the particular frequency, the IMD automatically will switch to a safe mode of operation (step 906). Next, the IMD sets a predetermined time period and starts a timer (block 908). The IMD then will continue to monitor the magnetic field and/or the RF signal amplitude at the predetermined frequency (blocks 910). If the magnetic field continues to exceed the predetermined strength and the RF signal continues to exceed the predetermined amplitude, the predetermined time period is extended by an incremental amount (block 912). Otherwise, the time period is not extended. Next, the timer is checked to determine if it has reached or passed the predetermined time period (decision block 914). If not, steps 910-914 are repeated. If the timer has reached or passed the predetermined time period, then the IMD will automatically switch back to its normal mode of operation (block 916).

Figure 10:
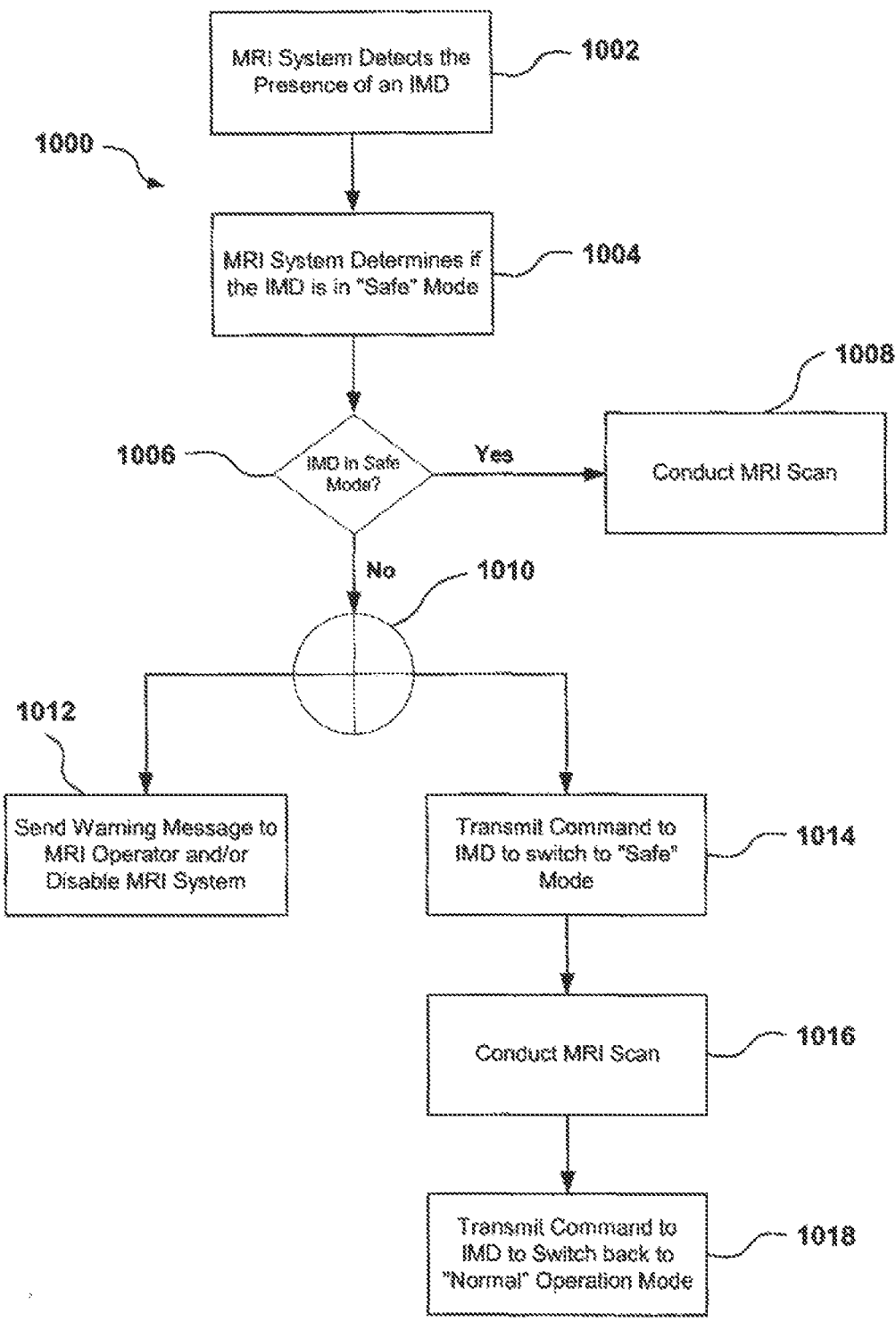

Referring now to FIG. 10, flow chart 1000 illustrates yet another embodiment of a method for safely operating an IMD in the presence of an MRI system. In accordance with this particular embodiment, the MRI system (e.g., MRI system 130 in FIG. 1) detects the presence of an IMD (block 1002). As discussed above, a telemetry system (e.g., telemetry system 140 in FIG. 1) associated with the MRI system can detect IMDs using wireless communications, such as near field and/or far field RF telemetry. Alternatively, in another embodiment, instead of the telemetry system detecting the presence of the IMD, the IMD can be operable to detect the presence of an MRI magnetic field and then communicate with the telemetry system associated with the MRI system, informing the MRI system that the IMD is present.

Once the MRI System and the IMD initiate communications, the MRI system can receive information about the IMD via the telemetry link. In one embodiment, the MRI system receives at least some data from the IMD indicating whether the IMD is in a safe mode of operation, as defined above (block 1004). If the IMD is in a safe mode of operation (decision block 1006), the MRI system can proceed with an MRI scan (block 1008). Alternatively, if the IMD is not in a safe mode of operation, one or more functions may occur (which is illustrated as alternative block 1010).

In one embodiment, if the IMD is not in a safe mode of operation, the MRI system or the telemetry system associated with the MRI system can send an alarm message to the MRI operator, informing the operator that a non-safe IMD is present (block 1012). Alternatively, in another embodiment, instead of sending an alarm message to the MRI operator, the MRI system can be operable to automatically prevent MRI scans from occurring when an IMD is present, but not in a safe mode of operation (block 1012). In yet another embodiment, the MRI system can be operable to send an alarm and disable MRI scan functionality.

In yet another embodiment of the invention, if an IMD is not in a safe mode of operation, the MRI system and/or the telemetry system associated with the MRI can transmit a command wirelessly to the IMD instructing it to switch to a safe mode of operation (block 1014). After the IMD switches to a safe mode of operation, the MRI system then can conduct an MRI scan (1016). In some embodiment, the telemetry system and/or the MRI system will wait for a message from the IMD confirming that the IMD switched to a safe mode of operation prior to conducting the MRI scan. Upon completion of the MRI scan, the MRI system, then can send a command to the IMD instructing it to switch back to its normal mode of operation, which the IMD will do upon receiving the command (block 1018).

In conclusion, the present invention provides novel systems, methods and devices for mitigating the hazards associated with using IMDs in the presence if EMI, and in particular, in MRI environments. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. An implantable medical device comprising:
    a detector configured to sense a MRI electromagnetic field;
    communications circuitry configured to receive a command from an external device; and
    memory and a processor configured to:
        switch operation of the implantable medical device from a non-MRI mode to an MRI mode upon reception of the command by the communications circuitry outside the presence of the MRI electromagnetic field, and
        while in the MRI mode, switch operation of the implantable medical device from a first mode of operation to a second mode of operation based on the MRI electromagnetic field being detected, wherein the implantable medical device is prohibited from switching operation from the first mode to the second mode while operating in the non-MRI mode.

2. The device of claim 1, wherein the processor is further configured to:
    measure a time period from when operation of the implantable medical device is switched to the second mode; and
    switch the implantable medical device from the second mode to the first mode when the measured time period reaches a predetermined time period.

3. The device of claim 2, wherein the predetermined time period is extended if the MRI electromagnetic field is detected at the end of the predetermined time period.

4. The device of claim 1, wherein the implantable medical device is a cardiac pacing device.

5. The device of claim 1, wherein the implantable medical device is an implantable cardioverter defibrillator.

6. The device of claim 1, wherein the first mode comprises delivering a rate-responsive therapy and the second mode comprises delivering a non-rate-responsive therapy.

7. The device of claim 1, wherein the first mode comprises delivering a demand pacing therapy and the second mode comprises delivering a non-demand pacing therapy.

8. The device of claim 1, wherein arrhythmia detection is enabled in the first mode and turned-off in the second mode.

9. The device of claim 1, wherein the processor is configured to detect the cessation of the MRI electromagnetic field via the detector and switch operation of the implantable medical device from the second mode back to the first mode based on the detection of the cessation of the MRI electromagnetic field.

10. The device of claim 1, wherein the processor is configured to switch operation of the implantable medical device from the MRI mode back to the non-MRI mode based on reception of a second command by the communications circuitry.

11. The device of claim 1, wherein the processor is configured to detect the MRI electromagnetic field based on the strength of the MRI electromagnetic field exceeding a predetermined field strength threshold.

12. A method of operating an implantable medical device comprising:
    receiving a command from an external device;
    switching, upon receiving the command, operation of the implantable medical device from a non-MRI mode to an MRI mode prior to a MRI scan while outside the presence of an MRI electromagnetic field, and
    detecting the MRI electromagnetic field of the MRI scan with a detector of the implantable medical device while the implantable medical device operates in the MRI mode; and
    switching operation of the implantable medical device from a first mode of operation to a second mode of operation based on the MRI electromagnetic field being detected, wherein the implantable medical device is prohibited from switching operation from the first mode to the second mode while operating in the non-MRI mode.

13. The method of claim 12, further comprising:
    measuring a time period from when operation of the implantable medical device is switched to the second mode; and
    switching the implantable medical device from the second mode to the first mode when the measured time period reaches a predetermined time period.

14. The method of claim 13, wherein the predetermined time period is extended if the MRI electromagnetic field is detected at the end of the predetermined time period.

15. The method of claim 12, wherein the implantable medical device is one or both of a cardioverter defibrillator and a cardiac pacing device.

16. The method of claim 12, wherein the first mode comprises delivering a rate-responsive therapy and the second mode comprises delivering a non-rate-responsive therapy.

17. The method of claim 12, wherein the first mode comprises delivering a demand pacing therapy and the second mode comprises delivering a non-demand pacing therapy.

18. The method of claim 12, wherein arrhythmia detection is enabled in the first mode and turned off in the second mode.

19. The method of claim 12, further comprising:
    detecting the cessation of the MRI electromagnetic field with the detector; and
    switching operation of the implantable medical device from the second mode back to the first mode based on the detection of the cessation of the MRI electromagnetic field.

20. The method of claim 12, wherein the MRI electromagnetic field is detected based on the strength of the MRI electromagnetic field exceeding a predetermined field strength threshold.

* * * * *